United States Patent [19]

Hvid

[11] Patent Number: Plant 6,377

[45] Date of Patent: Nov. 8, 1988

[54] BEGONIA PLANT NAMED 'NANCY'

[75] Inventor: Soeren Hvid, Aarup, Denmark

[73] Assignee: L. Daehnfeldt A/S, Odense, Denmark

[21] Appl. No.: 871,634

[22] Filed: Jun. 6, 1986

[51] Int. Cl.[4] ..... A01H 5/00

[52] U.S. Cl. ..... Plt./68

[58] Field of Search ..... Plt./68

*Primary Examiner*—James R. Feyrer

*Attorney, Agent, or Firm*—Olson and Olson

[57] ABSTRACT

A new and distinctive cultivar of begonia plant particularly characterized by its vigorous, compact growth habit, pure white tepals that maintain color even under high light conditions, its floriferous display, and by its excellent keeping qualities.

2 Drawing Sheets

BACKGROUND OF THE INVENTION

This invention relates to a new and distinctive cultivar of begonia plant known botanically as *Begonia hiemalis* Begonia (Fotsch) and known by the cultivar name Nancy.

This new cultivar was discovered by me as a mutation of Barbara, U.S. Plant Pat. No. 5,179, observed in a group of plants.

Asexual reproduction by stem and/or leaf cuttings has reproduced the unique features of the new cultivar through successive propagations.

The following characteristics distinguish the new begonia from both its parents and other begonias commercially known and used in the floriculture industry:

(1) The new cultivar shows no pubscense on the foliage. The plant is vigorous and compact.

(2) Compared to Barbara, which has rose flowers, Nancy has completely white flowers and white buds.

(3) The new cultivar is double with many flowers having 2-3 and sometimes four whorls of tepals in the center of the flower. The flowers seldom appear to be old.

(4) The new cultivar is considered to be highly floriferous. The stems on which flowering occurs tend to have initiation and development at several nodes at one time.

(5) The keeping qualities of the flowers and the foliage in all seasons allows production and sales efficiencies to be maximized.

(6) The new cultivar tends to be very vigorous so that 10 cm. pot production is best done with shoot cuttings and tip pinching.

(7) Propagation by leaf cuttings is difficult under light and high temperatures in summer months. Stem cuttings can readily be produced in this season.

(8) Nancy is very superior with respect to color and keeping qualities of winter crops of hiemalis begonias.

THE DRAWING

The accompanying two color photographs illustrate the overall appearance of this cultivar taken as a face view of the plant and individual leaf, buds and flower, respectively, showing the colors as true as it is reasonably possible to obtain in a colored reproduction of this type.

DESCRIPTION OF THE NEW VARIETY

The following is a detailed description of my new begonia cultivar based on plants produced under commercial practices in glasshouses in various places in Denmark. Color references are made to The Royal Horticultural Society Colour Chart, except where general color terms of ordinary dictionary significance are used.

Parentage: A mutation of the cultivar Barbara.

Propagation:

*Type cutting.*—Stem cutting.

*Time to root.*—27-30 days at 21° C. in summer; 25-28 days at 21° C. in winter.

*Rooting habit.*—Uniform, dentritic, fibrous.

*Time for shoot development of leaf cuttings.*—70-85 days to develop adventitious shoots 5-6 cm. (1.96-2.37 inches) long from stick date.

THE PLANT

Form: Low bush type, self-branching, herbaceous.

Habit of growth: Generally rapid, vigorous with strong stems, strong penduncles and strong pedicels.

Foliage: Leaves simple, alternate, borne on vigorous petioles, firm.

(1) *Size.*—Average leaf at maturity from 10-12 cm. (3.9-4.75 inches) long. Leaves may be larger or smaller depending on density of leaf canopy.

(2) Shape.—Ovate, slightly concave.

(3) Texture.—Leaf is firm, top glabrous, underside rugose.

(4) Margin.—Crenate.

(5) Color.—Young foliage top side; green 137 D, under side; yellow-green 146 D. Mature foliage top side; yellow-green 147 A to green 139, under side; yellow-green 147 C to 148 A.

(6) *Veination.*—Palmate.

THE FLOWER

Flowering habits: Flowering in racemes, with several clusters arising from the stem nodes at the same time giving a highly floriferous appearance. Flowering is continuous for a long period of time.

Natural flowering season: Flowering occurs naturally with shortened days lengths beginning mid-September and continuing through May. Reducing day length in summer speeds up flower initiation.

Flower bud: Flat, round, white with a shade of light green.

Flowers borne: On vigorous penduncles and pedicles in a raceme. The extra doubleness of the flowers causes a pendulous appearance because of the weight of the flowers.

Quantity: Very floriferous, often having 18–20 flowers per main stem in flowering stage at one time.

Tepals:

(1) *Shape.*—Nearly circular.

(2) *Color.*—Top side in winter when opening: R.H.S. 155 B; fading to: R.H.S. 155 D; under side: R.H.S. 155 B.

(3) *Number.*—16–32.

(4) *Size.*—4 Basal tepals 25–30 mm (1.0–1.2 inch), interior tepals 10–20 mm (0.4–0.75 inch).

(5) *Flower size.*—Up to 5 cm (2 inches) in diameter.

*Reproductive organs.*—Stamens: sterile triploid hybrid.

Disease resistance: No particular increase in resistance to disease observed to date.

I claim:

1. A new and distinct cultivar of *Begonia hiemalis* plant named Nancy, as shown and described, and particularly characterized by its vigorous, compact growth habit; pure white tepals that maintain color even under high light conditions; floriferous habit; and by its excellent keeping qualities.

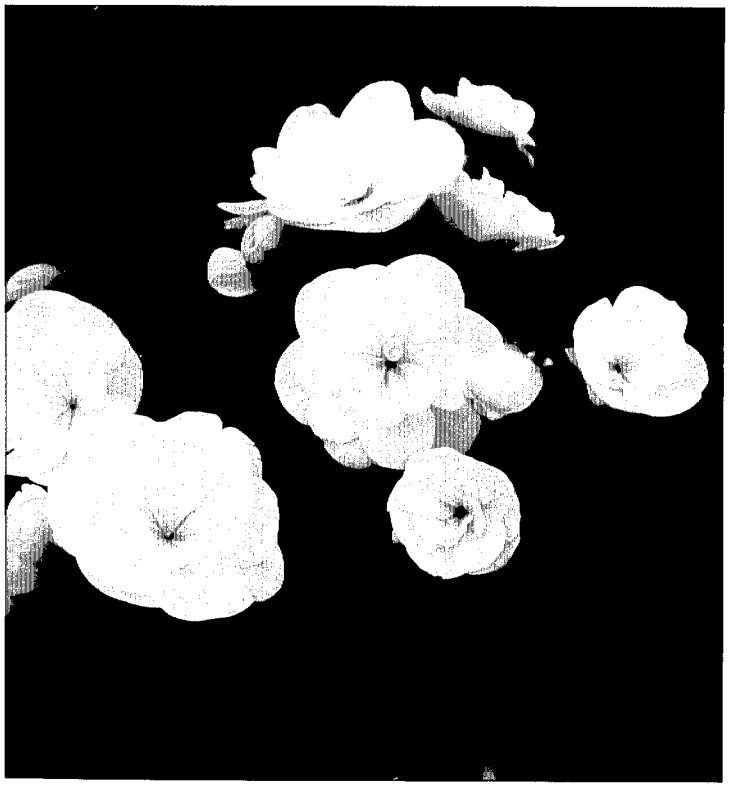

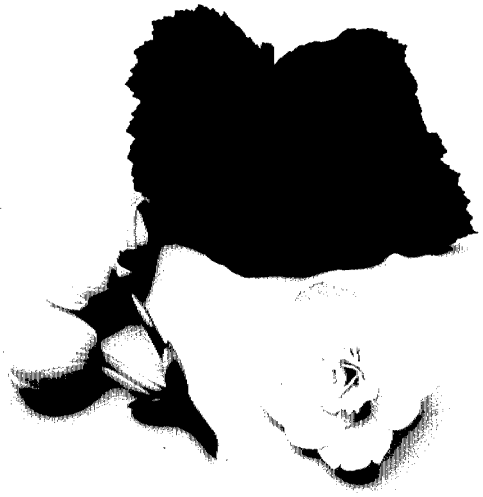

* * * * *